US009149456B2

(12) United States Patent
Holmes et al.

(10) Patent No.: US 9,149,456 B2
(45) Date of Patent: Oct. 6, 2015

(54) LAIDLOMYCIN COMPOSITIONS AND METHODS

(75) Inventors: Steven Holmes, Tinley Park, IL (US); Janice Cacace, Miami, FL (US)

(73) Assignee: Zoetis Services LLC, Florham Park, NJ (US)

( * ) Notice: Subject to any disclaimer, the term of this patent is extended or adjusted under 35 U.S.C. 154(b) by 6 days.

(21) Appl. No.: 12/456,300

(22) Filed: Jun. 15, 2009

(65) Prior Publication Data

US 2010/0022634 A1    Jan. 28, 2010

Related U.S. Application Data

(60) Provisional application No. 61/084,016, filed on Jul. 28, 2008.

(51) Int. Cl.
| *A61K 31/35* | (2006.01) |
| *A23K 1/00* | (2006.01) |
| *A23K 1/17* | (2006.01) |
| *A23K 1/18* | (2006.01) |

(52) U.S. Cl.
CPC ............. *A61K 31/35* (2013.01); *A23K 1/002* (2013.01); *A23K 1/17* (2013.01); *A23K 1/1813* (2013.01)

(58) Field of Classification Search
None
See application file for complete search history.

(56) References Cited

U.S. PATENT DOCUMENTS

| 4,015,972 A * | 4/1977 | Watkins et al. .................... 71/31 |
| 4,148,890 A | 4/1979 | Czok et al. |
| 4,394,377 A | 7/1983 | Spires |
| 4,405,609 A | 9/1983 | Potter |
| 4,431,665 A | 2/1984 | Kluge et al. |
| 4,478,935 A | 10/1984 | Williams et al. |
| 4,542,027 A | 9/1985 | Clark |
| 4,582,853 A | 4/1986 | Liu et al. |
| 4,617,294 A * | 10/1986 | Krivak et al. ................... 514/52 |
| 4,824,863 A | 4/1989 | Hamill et al. |
| 4,933,364 A | 6/1990 | Ivy et al. |
| 5,019,148 A * | 5/1991 | Moore ............................. 71/11 |
| 5,047,338 A | 9/1991 | Miescher et al. |
| 5,049,495 A | 9/1991 | Miescher et al. |
| 5,152,995 A | 10/1992 | Runkel et al. |
| 5,273,752 A | 12/1993 | Ayer |
| 5,462,741 A | 10/1995 | Carr |
| 5,541,224 A | 7/1996 | O'Doherty |
| 5,686,125 A * | 11/1997 | Mueller .......................... 426/74 |
| 5,874,103 A | 2/1999 | Moore et al. |
| 6,255,505 B1 | 7/2001 | Bijl et al. |
| 6,365,174 B1 | 4/2002 | Lowe et al. |
| 6,387,412 B1 * | 5/2002 | Moore .......................... 424/490 |
| 6,441,208 B2 | 8/2002 | Bijl et al. |
| 6,458,377 B1 | 10/2002 | Lowe et al. |
| 6,727,373 B2 | 4/2004 | Bijl et al. |
| 7,416,742 B2 | 8/2008 | McNeff et al. |
| 2001/0025114 A1 | 9/2001 | Bijl et al. |
| 2003/0143659 A1 | 7/2003 | Bijl et al. |
| 2003/0152689 A1 | 8/2003 | Ethington |
| 2004/0071782 A1 | 4/2004 | Agnew et al. |
| 2004/0247568 A1 | 12/2004 | Guerino |
| 2006/0003022 A1 | 1/2006 | McNeff et al. |
| 2006/0141098 A1 * | 6/2006 | Persson et al. ................... 426/72 |
| 2007/0116729 A1 | 5/2007 | Palepu |
| 2008/0274211 A1 | 11/2008 | McNeff et al. |

FOREIGN PATENT DOCUMENTS

| EP | 0024189 | 2/1981 | |
| NZ | 503578 | 1/2003 | |
| WO | 2008/123898 A1 * | 10/2008 | ............... A23K 1/00 |
| WO | 2009/149012 | 12/2009 | |

OTHER PUBLICATIONS

"Rate of Gain, Feed Efficiency, and Carcass Quality of Finishing Steers Fed Different Levels of Laidlomycin Propionate," by Fontenot et al., Animal Science Research Report (Virginia Polytechnic Institute and State University, Virginia Agricultural Experiment Station) 124-26 (1987/1988).*
"Excipients" in Remington: The Science and Practice of Pharmacy, 21st Ed. By Tory et al. (Eds.), Lippincott Williams & Wilkins (Philadelphia), p. 317 (2006).*
Extended European Search Report dated Jul. 9, 2012 (EP09803229. 5), 5 pages.
Database WPI Week 200358, Thomson Scientific, London, GB; AN 2003-615117 (Mar. 9, 2012), 5 pages.
RK McGuffey et al. Ionophores for Dairy Cattle: Current Status and Future Outlook, J. Dairy Sci. 84 (E Suppl.): E194-E203, (2001).

\* cited by examiner

*Primary Examiner* — Theodore R West
(74) *Attorney, Agent, or Firm* — Martha A. Gammill

(57) ABSTRACT

An animal feed additive composition comprises an effective amount of a laidlomycin, a carrier, magnesium sulfate, and silicon dioxide. Other embodiments include methods of making the animal feed additive compositions, and the use of a laidlomycin in the manufacture of an animal feed additive for increasing the efficiency of feed utilization and rate of weight gain in domestic animals.

26 Claims, No Drawings

LAIDLOMYCIN COMPOSITIONS AND METHODS

CROSS REFERENCE TO RELATED APPLICATIONS

This application claims priority to the filing date of U.S. Provisional Application No. 61/084,016 filed Jul. 28, 2008; the disclosure of which is incorporated by reference.

BACKGROUND

There are many different species of ruminant animals found around the world. Ruminants include cattle, sheep, goats, buffalo, deer, and elk. These animals have a digestive system uniquely different from other animals (including humans, chickens, and pigs). Instead of having only one compartment to the stomach, ruminants have four compartments. The rumen is the largest section of the stomach and is the main digestive area. The rumen is filled with billions of microorganisms that are able to break down grass and other coarse vegetation that animals having one stomach cannot digest.

Laidlomycin is a known antibiotic that has been shown to inhibit the growth of Gram positive bacteria. Laidlomycin has also been shown to increase the efficiency of feed utilization and rate of weight gain in domestic animals, especially meat-producing and milk-producing animals, such as cattle. Carbohydrates form a large part of these animals' diets, and the efficiency of carbohydrate utilization is desirably increased by treatment which encourages intraruminal production of propionate rather than acetate from carbohydrates. Additionally, laidlomycin suppresses rumen lactic acid production, thereby assisting in the prevention or treatment of bloat in ruminant animals.

Animal feedstuff compositions containing a therapeutic and/or prophylactic level of laidlomycin have been prepared by admixing the drug or a salt thereof with the feedstuff directly or by admixing an additive containing the drug with the desired feedstuff. Feed additives are normally prepared by admixing the drug or salt thereof, or a solution of the drug or a salt thereof with an edible substrate such as corn cob grits, soybean feed, corn meal or the like. Typically, laidlomycin is prepared by fermentation of organisms such as *Streptoverticillium eurocidicum*.

There remains a need for alternative feed additive compositions comprising laidlomycin.

BRIEF SUMMARY

The above-described and other drawbacks are alleviated by an animal feed additive composition comprising an effective amount of laidlomycin, a carrier, magnesium stearate, and silicon dioxide.

Another embodiment includes the use of a laidlomycin in the manufacture of a feed additive increasing the efficiency of feed utilization in domestic animals. The feed additive comprises an effective amount of laidlomycin, a carrier magnesium stearate, and silicon dioxide.

In another embodiment, an animal feed composition comprises an animal foodstuff, and an effective amount of an animal feed additive composition comprising an effective amount of laidlomycin, a carrier, magnesium stearate, and silicon dioxide.

In another embodiment, a method of making an animal feed additive composition, comprises forming a mixture comprising 5 wt % to 20 wt % of a laidlomycin, 73 wt % to 94 wt % of a carrier, 0.5 wt % to 5 wt % of magnesium stearate, and 0.5 wt % to 2.0 wt % of silicon dioxide, wherein all amounts are based on the total weight of the animal feed additive; and granulating the mixture to form a granulate, wherein granulating comprises roll compacting, milling and screening.

The above-described and other features will be appreciated and understood by those skilled in the art from the following detailed description, drawings, and appended claims.

DETAILED DESCRIPTION

Disclosed herein are animal feed additive compositions comprising laidlomycin, magnesium stearate, and silicon dioxide. A "feed additive" composition refers to a composition suitable for incorporation into the diet of an animal through incorporation into the animal's food and/or water. In one embodiment, the animal feed additive is in the form of a granulate. Feed additive compositions are also referred to as feed "pre-mix" compositions.

Since laidlomycin propionate potassium is the reference standard for laidlomycin feed grade materials, all laidlomycin concentrations and percentages stated herein, unless indicated otherwise, are calculated as the propionate potassium equivalent, regardless of the form present (e.g., the free base, complexes or salts other than the propionate potassium salt, etc.) Laidlomycin is typically prepared by fermentation of *Streptoverticillium eurocidicum*, followed by extraction to produce a fermentation product containing 90% or more laidlomycin, specifically 90 wt % to 102 wt % laidlomycin A+B. In one embodiment, the laidlomycin has an alpha laidlomycin activity of greater than 80 wt % and a beta laidlomycin activity of not greater than 20 wt %.

The laidlomycin comprises 5 wt % to 20 wt % of the total weight of the laidlomycin animal feed additive composition, specifically 8 wt % to 15 wt % laidlomycin animal feed additive composition and more specifically 11 wt % to 11.55 wt % laidlomycin animal feed additive composition.

The laidlomycin animal feed additive composition also comprises silicon dioxide and magnesium stearate. The silicon dioxide is believed to act as a flow aid while the magnesium stearate acts as a binder. Unexpectedly, the synergistic combination of silicon dioxide and the magnesium stearate produces a harder and more stable granulate than other excipient combinations. The silicon dioxide comprises 0.5 wt % to 5.0 wt % of the total weight of the laidlomycin animal feed additive composition, specifically 0.5 wt % to 2.0 wt % of the laidlomycin animal feed additive composition.

The laidlomycin animal feed additive composition also comprises a particulate carrier. As used herein, a particulate carrier is typically a carrier having a diameter of 1 to 50 microns. Suitable particulate carriers include mineral carriers comprising one or more mineral salts, organic carriers, and combinations thereof. Suitable particulate mineral carriers include, for example, dicalcium phosphate, calcium sulfate, calcium carbonate, and combinations comprising one or more of the foregoing carriers. Suitable organic carriers include starch, sucrose, glucose, mannitol, sorbitol, dextrose and combinations comprising one or more of the foregoing carriers. In one embodiment, the carrier comprises calcium sulfate or calcium carbonate.

The carrier typically comprises 73 wt % to 94 wt % of the total weight of the laidlomycin animal feed additive composition, specifically 81 wt % to 88 wt % of the laidlomycin animal feed additive composition.

In one embodiment, the composition has a pH from about 7.0 to 8.0. In another embodiment, a method of making an animal feed additive composition, comprises forming a mixture comprising 5 wt % to 20 wt % of a laidlomycin, 73 wt % to 94 wt % of a carrier, 0.5 wt % to 5 wt % of magnesium stearate, and 0.5 wt % to 2.0 wt % of silicon dioxide, wherein all amounts are based on the total weight of the animal feed additive composition.

In another embodiment, an animal feed additive composition consists essentially of 5 wt % to 20 wt % of a laidlomycin, 73 wt % to 94 wt % of a carrier, 0.5 wt % to 5 wt % of magnesium stearate, and 0.5 wt % to 2.0 wt % of silicon dioxide, wherein all amounts are based on the total weight of the animal feed additive composition.

In another embodiment, an animal feed additive composition consists of 5 wt % to 20 wt % of a laidlomycin, 73 wt % to 94 wt % of a carrier, 0.5 wt % to 5 wt % of magnesium stearate, and 0.5 wt % to 2.0 wt % of silicon dioxide, wherein all amounts are based on the total weight of the animal feed additive composition.

In a preferred embodiment, an animal feed additive composition comprises about 11 wt % of laidlomycin, about 87 wt % of calcium sulfate, about 0.5 wt % magnesium stearate, and about 0.5 wt % silicon dioxide, wherein all amounts are based on the total weight of the animal feed additive composition.

In a preferred embodiment, an animal feed additive composition consists essentially of about 11 wt % of laidlomycin, about 87 wt % of calcium sulfate, about 0.5 wt % magnesium stearate, and about 0.5 wt % silicon dioxide, wherein all amounts are based on the total weight of the animal feed additive composition.

In a preferred embodiment, an animal feed additive composition consists of about 11 wt % of laidlomycin, about 87 wt % of calcium sulfate, about 0.5 wt % magnesium stearate, and about 0.5 wt % silicon dioxide, wherein all amounts are based on the total weight of the animal feed additive composition.

The compositions optionally comprise additional agents such as anti-caking agents, flow agents and combinations thereof. Optionally the compositions comprise additional binding agents such as starches and sugars.

In one embodiment, the feed additive composition is stable when tested in a stress test. A specific stress test is exposure to 60° C. and 75% relative humidity for 8 weeks, and stable means less than 20% degradation of the laidlomycin in the formulation, specifically less than 15% degradation of the laidlomycin in the formulation.

The laidlomycin, a particulate carrier, magnesium stearate, and silicon dioxide are combined to form the animal feed additive composition. In one embodiment, the animal feed additive composition is a multiparticulate composition. The term multiparticulate is intended to refer broadly to small particles, such as a powder or fine granules, regardless of their composition or the manner in which they are formed. The particles generally are of a mean diameter of about 150 to 850 μM.

In one embodiment, the laidlomycin, carrier, magnesium stearate and silicon dioxide are granulated to form the animal feed additive composition. Granulation is a process by which relatively small particles are built up into larger granular particles. In wet-granulation, a liquid is used to increase the intermolecular forces between particles, leading to an enhancement in granular integrity, referred to as the "strength" of the granule. Often, the strength of the granule is determined by the amount of liquid that is present in the interstitial spaces between the particles during the granulation process. Examples of liquids found to be effective wet-granulation liquids include water, ethanol, isopropyl alcohol and acetone.

In an exemplary granulation process, the components of the animal feed additive are formed into a mixture and the mixture is dry roll compacted to form the granulate.

Several types of wet-granulation processes can be used to form laidlomycin-containing multiparticulates. Examples include fluidized bed granulation, rotary granulation and high-shear mixers. In fluidized bed granulation, air is used to agitate or "fluidize" particles of laidlomycin and/or carrier in a fluidizing chamber. The liquid is then sprayed into this fluidized bed, forming the granules. In rotary granulation, horizontal discs rotate at high speed, forming a rotating "rope" of laidlomycin and/or carrier particles at the walls of the granulation vessel. The liquid is sprayed into this rope, forming the granules. High-shear mixers contain an agitator or impeller to mix the particles of laidlomycin and/or carrier. The liquid is sprayed into the moving bed of particles, forming granules. In these processes, the liquid preferably comprises the magnesium stearate and silicon dioxide. Also in these processes, all or a portion of the carrier can be dissolved into the liquid prior to spraying the liquid onto the particles. Thus, in these processes, the steps of forming the liquid mixture and forming particles from the liquid mixture occur simultaneously.

In another embodiment, the particles are formed by extruding the liquid mixture into a solid mass followed by spheronizing or milling the mass. In this process, the liquid mixture, which is in the form of a paste-like plastic suspension, is extruded through a perforated plate or die to form a solid mass, often in the form of elongated, solid rods. This solid mass is then milled to form the multiparticulates. In one embodiment, the solid mass is placed, with or without an intervening drying step, onto a rotating disk that has protrusions that break the material into multiparticulate spheres, spheroids, or rounded rods. The so-formed multiparticulates are then dried in a Fluid bed dryer to remove any remaining liquid. This process is sometimes referred to in the pharmaceutical arts as an extrusion/spheronization/fluid bed drying process.

Once the particles are formed, a portion of the liquid is removed, typically in a drying step, thus forming the multiparticulates. Preferably, at least 80% of the liquid is removed from the particles, more preferably at least 90%, and most preferably at least 95% of the liquid is removed from the particle during the drying step.

The multiparticulates may also be made by a granulation process comprising the steps of (a) forming a solid mixture comprising laidlomycin, carrier, magnesium stearate, and silicon dioxide; and (b) granulating the solid mixture to form multiparticulates. Examples of such granulation processes include dry granulation and melt granulation, both well known in the art. See *Remington's Pharmaceutical Sciences* (18th Ed. 1990).

An example of a dry granulation process is roller compaction. In roller compaction processes, the solid mixture is compressed between rollers. The rollers can be designed such that the resulting compressed material is in the form of small beads or pellets of the desired diameter. Alternatively, the compressed material is in the form of a ribbon that may be milled to form multiparticulates using methods well known in the art.

In melt granulation processes, the solid mixture is fed to a granulator that has the capability of heating or melting the carrier. Equipment suitable for use in this process includes high-shear granulators and single or multiple screw extruders, such as those described above for melt-congeal processes. In melt granulation processes, the solid mixture is placed into the granulator and heated until the solid mixture agglomerates. The solid mixture is then kneaded or mixed until the desired particle size is attained. The so-formed granules are then cooled, removed from the granulator and sieved to the desired size fraction, thus forming the multiparticulates.

In another embodiment pin granulation is employed where a mixture is mixed in a pin mixer followed by granulation on a disc pelletizer and drying in a fluid bed dryer.

The administration of laidlomycin animal feed additive compositions and methods for increasing the efficiency of feed utilization in domestic animals are carried out in the normal manner. An oral administration is primarily suitable. The laidlomycin compositions may be mixed with feedstuffs or with drinking water.

The laidlomycin concentrations in feedstuffs or in drinking water may vary within certain limits, in general between 5.5 and 11 ppm of the laidlomycin in the feedstuff or drinking water. The concentration of laidlomycin is 5-11 g/ton in the final feed.

The laidlomycin concentrations are based on the feed or drinking water preparations ad lib, i.e., for free feed or drinking water consumption during a normal practical fattening or rearing period.

Manufactured foodstuffs for animals such as cattle, pigs, and fowl are usually provided in the form of pellets or similar particulate material. Pellets are typically manufactured by combining a cereal base with ingredients such as oil and protein, steam conditioning the mixture (for example at 70° C. for 5 minutes), extruding through a circular die (typically between 2 mm and 15 mm in diameter), cutting into appropriately sized lengths (e.g., 5-20 mm), and drying. The finished pellets are generally cylindrically shaped and have a relatively smooth surface.

In one embodiment, an animal feed composition is prepared by adding a laidlomycin animal feed additive as described herein (a "Type A" premix) composition to an animal foodstuff. These premixes are typically defined as Type B or Type C premixes. Type B or Type C premixes can be formed by adding a Type A premix to soybean hulls and grits, corncob hulls and grits, and rice hulls and grits are added as possible carriers. The laidlomycin animal feed additive composition may be added to the food in a number of ways. The laidlomycin animal feed additive composition containing a given quantity of laidlomycin may be added to a given quantity of feed and mixed or blended to provide a substantially homogeneous medicated feed composition. Large feed lots may be prepared in this manner for treating a large number of animals. Alternatively, feed batches containing feed for a single animal or single meal may be prepared either by mixing a predetermined quantity of laidlomycin animal feed additive composition with the animal feed or by adding a predetermined quantity of premix to an animal's feed as a top dressing.

The treatment method can also be extended to other methods for treating and feeding livestock. Thus, for example, the laidlomycin animal feed additive compositions may be combined with other active substances, such as, for example, with anti-coccidial agents, growth-promoting agents, antiparasitics, or antibiotics.

The invention is further illustrated by the following non-limiting examples.

EXAMPLES

TABLE 1

| Component | Composition 1 | Composition 2 | Composition 3 | Composition 4 |
|---|---|---|---|---|
| Laidlomycin | 11.0 | 11.0 | 11.0 | 11.0 |
| Silicon dioxide | 0.5 | 0.5 | 0.5 | 0.5 |
| Magnesium stearate | 0.5 | 0.75 | 0.75 | 0.75 |
| Calcium hydroxide | 0 | 10.0 | 0 | 0.1 |
| Calcium sulfate carrier | 88.0 | 77.75 | 87.75 | 87.65 |

The stability of the above four samples in of laidlomycin feed additive (Table 1) was determined under stress conditions of 60° C. and 75% relative humidity for eight (8) weeks. The amount of laidlomycin was measured by HPLC analysis. The stability data for the test batch formulation are shown in Table 2. As can be seen from Table 2, through 8 weeks under stress conditions, the laidlomycin animal feed additive is stable.

TABLE 2

| Time (weeks) | Example 1 | Example 2 | Example 3 | Example 4 |
|---|---|---|---|---|
| 0 | 11.65 | 11.13 | 11.30 | 11.37 |
| 1 | 11.29 (96.9%) | 9.88 (88.7%) | 10.74 (95.1%) | 10.87 (95.6%) |
| 2 | 10.85 (93.1%) | 9.94 (89.3%) | 11.00 (97.4%) | 11.04 (97.1%) |
| 4 | 10.48 (90.0%) | 9.52 (85.5%) | 10.01 (88.6%) | 10.15 (89.3%) |
| 6 | 10.48 (90.0%) | 9.65 (86.7%) | 10.13 (89.6%) | 10.08 (88.7%) |
| 8 | 10.04 (86.2%) | 9.28 (83.4%) | 9.49 (84.0%) | 9.45 (83.1%) |

Advantages of the animal feed additives disclosed herein are good particle size distribution, pH in good range for laidlomycin, flowability, and stability.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

All cited patents, patent applications, and other references are incorporated herein by reference in their entirety.

The invention claimed is:

1. An animal feed additive composition comprising:
   5 wt % to 20 wt % of laidlomycin,
   73 wt % to 94 wt % of calcium sulfate,
   0.5 wt % to 5.0 wt % of magnesium stearate, and
   0.5 wt % to 2.0 wt % of silicon dioxide
   wherein all amounts are based on the total weight of the animal feed additive composition and wherein the laidlomycin, calcium sulfate, magnesium stearate and silicon dioxide are formed into a mixture.

2. The animal feed additive composition of claim 1 in the form of a granulate.

3. The animal feed additive composition of claim 1 wherein the laidlomycin is at least 80% laidlomycin A.

4. The animal feed additive composition of claim 3 wherein the composition has a pH of 7.0 to 8.0.

5. The animal feed additive composition of claim 3 wherein the composition has a stability such that after exposure to 60° C. and 75% relative humidity carrier for 8 weeks, less than 20 wt % of the laidlomycin in the composition is degraded.

6. The animal feed additive composition of claim 5 wherein the degradation of laidlomycin is measured by HPLC.

7. An animal feed additive composition comprising:
   about 11 wt % laidlomycin,
   about 87 wt % calcium sulfate,
   about 0.5 wt % magnesium stearate, and
   about 0.5 wt % silicon dioxide
   wherein all amounts are based on the total weight of the animal feed additive composition and wherein the laidlomycin, calcium sulfate, magnesium stearate and silicon dioxide are formed into a mixture.

8. The animal feed additive composition of claim 7 wherein the laidlomycin is at least 80% laidlomycin A.

9. The animal feed additive composition of claim 7 wherein the composition has a pH of 7.0 to 8.0.

10. The animal feed additive composition of claim 7 wherein the composition has a stability such that after exposure to 60° C. and 75% relative humidity carrier for 8 weeks, less than 20 wt % of the laidlomycin in the composition is degraded.

11. The animal feed additive composition of claim 10 wherein the degradation of laidlomycin is measured by HPLC.

12. An animal feed additive composition comprising:
    An animal foodstuff and
    11 wt % to 11.5 wt % of laidlomycin,
    73 wt % to 94 wt % of calcium sulfate,
    0.5 wt % to 5.0 wt % of magnesium stearate, and
    0.5 wt % to 2.0 wt % of silicon dioxide
    wherein all amounts are based on the total weight of the animal feed additive composition and wherein the laidlomycin, calcium sulfate, magnesium stearate and silicon dioxide are formed into a mixture.

13. The animal feed composition of claim 12 wherein the animal foodstuff is suitable for cattle.

14. The animal feed composition of claim 12 wherein the laidlomycin is at least 80% laidlomycin A.

15. The animal feed composition of claim 12 wherein the composition has a pH of 7.0 to 8.0.

16. A method of making an animal feed additive composition comprising forming a mixture comprising:
    5 wt % to 20 wt % of laidlomycin,
    73 wt % to 94 wt % of calcium sulfate,
    0.5 wt % to 5.0 wt % of magnesium stearate, and
    0.5 wt % to 2.0 wt % of silicon dioxide
    wherein all amounts are based on the total weight of the animal feed additive; and granulating the mixture to form a granulate.

17. The method of claim 16 wherein the laidlomycin is at least 80% laidlomycin A.

18. The method of claim 16 wherein the composition has a pH of 7.0 to 8.0.

19. The composition of claim 7 wherein the laidlomycin is in the form of laidlomycin propionate potassium.

20. A method of making multiparticulates of an animal feed additive comprising:
    (a) forming a solid mixture comprising about 11% laidlomycin, 73 wt % to 94 wt % of calcium sulfate, about 0.5% magnesium stearate, and about 0.5% silicon dioxide; and
    (b) granulating the solid mixture to form multiparticulates.

21. The method of claim 20 wherein the granulation step is performed by roller compaction.

22. The animal feed additive composition of claim 1 further comprising an active substance selected from the group consisting of anti-coccidial agents, growth promoting agents, antiparasitic agents, antibiotics or combinations thereof.

23. The animal feed additive composition of claim 1 further comprising one or more growth promoting agents.

24. The animal feed additive composition of claim 1 further comprising one or more antibiotics.

25. The animal feed additive composition of claim 1 further comprising one or more anti-coccidial agents.

26. The animal feed additive composition of claim 1 further comprising one or more antiparasitic agents.

* * * * *